United States Patent [19]

Umino et al.

[11] 4,324,800
[45] Apr. 13, 1982

[54] NOVEL BENZYLALCOHOL DERIVATIVES AND PROCESSES FOR PREPARING SAME

[75] Inventors: Norihide Umino, Ageo; Tokuro Ohishi, Shakujii; Muneyoshi Ikezaki, Takarazuka; Masanori Sato, Kuki; Taku Nagao, Tokyo, all of Japan

[73] Assignee: Tanabe Seiyaku Co., Ltd., Japan

[21] Appl. No.: 243,246

[22] Filed: Mar. 12, 1981

[30] Foreign Application Priority Data

Mar. 28, 1980 [JP] Japan .................................. 55-41091

[51] Int. Cl.³ .................... A61K 31/24; C07C 69/017; C07C 69/78
[52] U.S. Cl. ...................................... 424/308; 424/311; 424/312; 560/108; 560/138; 560/27; 260/404
[58] Field of Search ................ 560/108, 138; 260/404; 424/308, 311, 312, 316

[56] References Cited

U.S. PATENT DOCUMENTS

| | | | |
|---|---|---|---|
| 3,657,244 | 4/1972 | Meatrup et al. | 560/138 |
| 4,010,191 | 3/1977 | Thiele et al. | 560/138 |
| 4,032,575 | 6/1977 | Ikezaki et al. | 260/501.11 |
| 4,093,814 | 6/1978 | Hauck et al. | 560/108 |
| 4,115,585 | 9/1978 | Manghisi et al. | 560/138 |
| 4,130,658 | 12/1978 | Nedelec et al. | 560/108 |

OTHER PUBLICATIONS

Wilson, Textbook of Organic Medical & Pharmaceutical Chemistry, pp. 39, 40 (1954).

*Primary Examiner*—G. T. Breitenstein
*Attorney, Agent, or Firm*—Bierman & Bierman

[57] ABSTRACT

A compound of the formula:

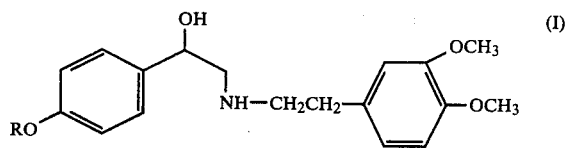

wherein R is alkanoyl of one to 20 carbon atoms, benzoyl or lower alkyl-benzoyl, and processes for preparation thereof are disclosed. Said compound (I) and a pharmaceutically acceptable acid addition salt thereof are useful as a cardiotonic agent.

9 Claims, No Drawings

NOVEL BENZYLALCOHOL DERIVATIVES AND PROCESSES FOR PREPARING SAME

This invention relates to a novel benzylalcohol derivative and processes for preparing same. More particularly, it relates to an α-(3,4-dimethoxyphenethylaminomethyl)-4-acyloxybenzylalcohol of the formula:

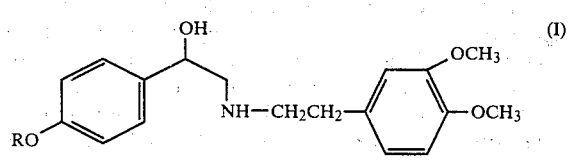

wherein R is alkanoyl of one to 20 carbon atoms, benzoyl or lower alkyl-benzoyl, or a pharmaceutically acceptable acid addition salt thereof.

The benzylalcohol derivative (I) of the present invention shows potent and long-lasting cardiac contractile activity and is useful as a cardiotonic agent. In particular, said derivative is characterized by its long-lasting cardiac contractile activity without substantial increase in the heart rate and other undesirable side effects.

Examples of the benzylalcohol derivative of the present invention include those of the formula (I) in which R is alkanoyl of one to 20 carbon atoms such as acetyl, propionyl, butyryl, isobutyryl, valeryl, isovaleryl, pivaloyl, caproyl, isocaproyl, heptanoyl, octanoyl, nonanoyl, decanoyl, lauroyl, myristoyl, palmitoyl, stearoyl or eicosanoyl; benzoyl; or lower alkyl-benzoyl such as o-toluoyl, m-toluoyl, p-toluoyl or p-ethylbenzoyl. Among them, a preferred subgenus include the benzylalcohol derivative of the formula (I) in which R is alkanoyl of 2 to 16 carbon atoms, benzoyl or methylbenzoyl. Further preferred subgenus is the benzylalcohol derivative of the formula (I) in which R is acetyl, pivaloyl, palmitoyl, benzoyl or p-toluoyl.

The benzylalcohol derivative (I) of the present invention can be used for pharmaceutical use as either the free base or a pharmaceutically acceptable acid addition salt thereof. The base and salt thereof are readily convertible from one to another by conventional methods, for example, by treating a solution of the free base with an acid or by neutralizing a solution of the acid addition salt with an alkali metal salt (e.g., potassium carbonate). Examples of the pharmaceutically acceptable acid addition salt include inorganic acid addition salts such as hydrochloride, sulfate, phosphate, nitrate and hydrobromide; and organic acid addition salts such as acetate, oxalate, succinate, benzoate, methanesulfonate and fumarate. The benzylalcohol derivative (I) and a pharmaceutically acceptable acid addition salt thereof may be administered either orally or parenterally, and may be further used in conjunction or admixture with a pharmaceutical excipient which is suitable for oral or parenteral administration. The excipient selected should be the one which does not react with the benzylalcohol derivative (I). Suitable excipients include, for example, arabic gum, gelatin, sorbit, tragacanth, polyvinylpyrrolidone, lactose, sucrose, potassium phosphate, magnesium stearate, talc, potato starch, corn starch and the like. The pharmaceutical preparation may be a solid dosage form such as tablets, pills, powder, capsules or granules, or a liquid dosage form such as a solution, an emulsion or a suspension. When administered parenterally, the benzylalcohol derivative (I) may be used in the form of an injection.

According to the present invention, the benzylalcohol derivative (I) can be prepared by condensing a N-protected α-(3,4-dimethoxyphenethylamino)acetophenone of the formula:

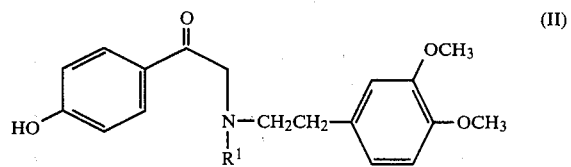

wherein $R^1$ is a protecting group, with a carboxylic acid compound of the formula:

R-OH     (III)

wherein R is the same as defined above, or a reactive derivative thereof to give a N-protected α-(3,4-dimethoxyphenethylamino)acetophenone of the formula:

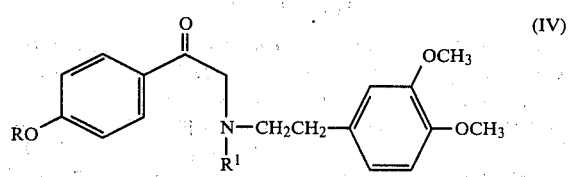

wherein R and $R^1$ are the same as defined above, and then subjecting said acetophenone (IV) to catalytic hydrogenation. Alternatively, the benzylalcohol derivative (I) may be prepared by treating the compound (IV) with a reducing agent to give a compound of the formula:

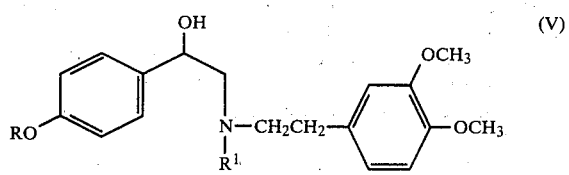

wherein R and $R^1$ are the same as defined above, and then subjecting said compound (V) to catalytic hydrogenation.

The above-mentioned reactions are shown by the following reaction scheme.

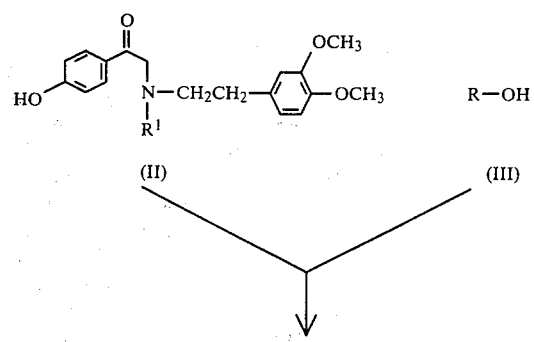

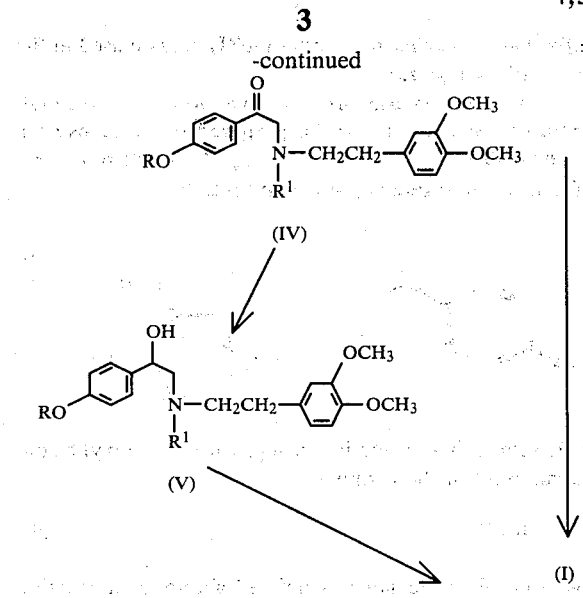

(In these formulae, R and R¹ are the same as defined above)

(II)+(III)→(IV)

In the above-mentioned reaction scheme, aralkyloxycarbonyl groups (e.g., benzyloxycarbonyl, p-methoxybenzyloxycarbonyl or p-methylbenzyloxycarbonyl) and aralkyl groups (e.g., benzyl or triphenylmethyl) can be preferably used as the protecting group (R¹). On the other hand, suitable examples of the starting compound (III) include an alkanoic acid of one to 20 carbon atoms such as acetic acid, butyric acid, isobutyric acid, valeric acid, isovaleric acid, pivalic acid, capronic acid, isocapronic acid, heptanoic acid, octanoic acid, nonanoic acid, decanoic acid, lauric acid, myristic acid, palmitic acid, stearic acid and eicosanoic acid; benzoic acid; and lower alkyl-benzoic acid such as o-, m- or p-toluic acid. Moreover, the reactive derivative of these carboxylic acid includes, for example, the corresponding acid halide, acid anhydride and the like.

The condensation reaction of the compound (II) with the compound (III) (free base) can be accomplished in the presence of a dehydrating agent in an inert solvent. Suitable examples of the dehydrating agent include dicyclohexylcarbodiimide, diisopropylcarbodiimide so forth. Chloroform, methylene chloride, ether, tetrahydrofuran and benzene are suitable as the inert solvent. It is preferred to carry out the reaction at a temperature of 0° C. to 30° C., especially at around 5° C. It is also preferred to carry it out in the presence of a trace of 4-dimethylaminopyridine because said pyridine serves to accelerate the reaction. On the other hand, the condensation reaction of the compound (II) with the acid halide of the compound (III) is readily conducted in the presence of an acid acceptor in an inert solvent. Chloroform, dimethylformamide and benzene are suitable as the solvent, and examples of the acid acceptor include organic and inorganic bases such as triethylamine, pyridine, sodium bicarbonate or sodium carbonate. This condensation reaction may be carried out without an acid acceptor if an organic base such as pyridine is used as the solvent. The reaction is preferably carried out at a temperature of 0° C. to 40° C. Moreover, the condensation reaction of the compound (II) with the acid anhydride of the compound (III) can be conducted in the presence of a catalytic amount of sulfuric acid or sodium acetate in an inert solvent. Chloroform, ether, tetrahydrofuran or pyridine are suitable as the solvent. It is preferred to carry out the reaction at a temperature of 0° C. to 100° C., especially at around 20° C.

(IV)→(V)

The compound (V) can be readily obtained by treating the N-protected α-(3,4-dimethoxyphenethylamino)acetophenone (IV) with a reducing agent in an inert solvent. Suitable examples of the reducing agent include an alkali metal borohydride (e.g., sodium borohydride, lithium borohydride), lithium aluminium hydride, diborane, sodium borohydride cyanide (NaBH₃CN) and the like. Ether, tetrahydrofuran, benzene, methanol and ethanol are suitable as the solvent. It is preferred to carry out the reaction at a temperature of 0° C. to 30° C., especially at around 0° C. If required, the compound (V) thus obtained may be purified in conventional manners, for example, by silica gel column chromatography.

(IV)→(I), and (V)→(I)

The catalytic hydrogenation of the compound (IV) or (V) can be readily conducted by dissolving said compound (IV) or (V) or an acid addition salt thereof in an inert solvent and shaking said solution in the presence of a catalyst in hydrogen atmosphere. The reaction may be carried out under either atmospheric pressure or increased pressure (e.g., one to 100 atomspheric pressure). Suitable examples of the catalyst include platinum, platinum oxide, palladium-black, palladium-carbon, colloidal palladium and the like. Lower alkanols (e.g., methanol, ethanol), water and ethyl acetate are suitable as the solvent. It is preferred to carry out the reaction at a temperature of 10° C. to 1002 C., especially at 10° to 50° C. In order to carry out the hydrogenation of the compound (IV) without side reactions, it is preferred to stop the reaction when 2 moles (per mole of the compound (IV)) of hydrogen uptake is completed. The benzylalcohol derivative (I) of the present invention can be readily separated from the reaction solution by filtering off the catalyst therefrom, condensing the filtrate to remove solvent, and then crystallizing or recrystallizing the residue obtained.

The starting compound (II) of the invention is readily obtained, for example, by subjecting α-(3,4-dimethoxyphenethylamino)-4-benzyloxyacetophenone hydrochloride (Japanese Patent Publication (examined) No. 10974/1978) to catalytic hydrogenation in an inert solvent to give α-(3,4-dimethoxyphenethylamino)-4-hydroxyacetophenone, and then introducing a protecting group into the nitrogen position of said 4-hydroxyacetophenone according to a per se known method such as Shotten-Baumann reaction.

Experiment

Male dogs weighing about 11 to 13 kg were anesthetized with sodium pentobarbital (30 mg/kg, i.v.). Under artificial respiration, the heart was exposed by thoractomy, and a calibrated strain gauge was attached to the wall of the left ventricle for oscillographical measurement of the ventricular contractile force. The heart rate was recorded by cardiotachography, triggered by arterial pulse. A test compound was injected into the left saphenous vein at a dose which induces about 30% increase in the ventricular contractile force.

The results are shown in the following Table.

TABLE

| Test compounds | Dose (μg/kg) | t ½*(sec. ± S.E.) |
|---|---|---|
| α-(3,4-dimethoxyphenethyl-aminomethyl)-4-p-toluoyloxy-benzylalcohol | 40 | 1495 ± 25 |
| α-(3,4-dimethoxyphenethyl-aminomethyl)-4-benzoyloxy-benzylalcohol | 39 | 1453 ± 43 |
| α-(3,4-dimethoxyphenethyl-aminomethyl)-4-pivaloyloxy-benzylalcohol | 37 | 1232 ± 71 |

Note:
*:Period of time in decreasing the cardiac contractile force to 50% of its maximum value.
:During the experiments, the increased heart rate was accounted less than 10 beats/minute.

EXAMPLE 1

(1) 44.2 g of α-(3,4-dimethoxyphenethylamino)-4-benzyloxyacetophenone hydrochloride were dissolved in 2 liters of methanol, and 5.0 g of 10% palladium-carbon were added thereto. The mixture was shaken at room temperature in hydrogen atmosphere under atmospheric pressure. After hydrogen uptake was completed, the mixture was filtered to remove the catalyst. The filtrate was evaporated to remove solvent, and the residue was recrystallized from methanol. 32.0 g of α-(3,4-dimethoxyphenethylamino)-4-hydroxyacetophenone were obtained. Yield: 90.9% M.p. 200° C.

(2) 30.0 g of α-(3,4-dimethoxyphenethylamino)-4-hydroxyacetophenone were dissolved in 500 ml of water, and 600 ml of chloroform were added thereto. 17.5 g of benzyloxycarbonyl chloride were added dropwise to the mixture under ice-cooling and stirring. During said dropwise addition of benzyloxycarbonyl chloride, a solution of 20.6 g of sodium bicarbonate in 500 ml of water was added dropwise thereto to keep said mixture under an alkaline condition. After said dropwise addition, the mixture was further stirred for 2 hours. Then, the chloroform layer was separated therefrom, washed with water and then evaporated to remove solvent. The residue obtained was recrystallized from methanol. 28.5 g of N-benzyloxycarbonyl-α-(3,4-dimethoxyphenethylamino)-4-hydroxyacetophenone were obtained as colorless needles. Yield: 74.4% M.p. 143°–144° C.

(3) 4.0 g of N-benzyloxycarbonyl-α-(3,4-dimethoxyphenethylamino)-4-hydroxyacetophenone were dissolved in 4 ml of pyridine, and 1.5 g of acetyl chloride were added dropwise thereto under ice-cooling. The mixture was stirred at room temperature for 2 hours. Then, the reaction mixture was poured into ice-water and extracted with ethyl acetate. The extract was washed with 10% hydrochloric acid and an aqueous sodium chloride solution, and evaporated to remove solvent. The residue thus obtained was recrystallized from ethanol. 4.2 g of N-benzyloxycarbonyl-α-(3,4-dimethoxyphenethylamino)-4-acetyloxyacetophenone were obtained as colorless needles. Yield: 96.1% M.p. 84°–86° C.

(4) 3.5 g of N-benzyloxycarbonyl-α-(3,4-dimethoxyphenethylamino)-4-acetyloxyacetophenone were dissolved in a mixture of 15 ml of tetrahydrofuran and 3 ml of methanol, and 0.27 g of sodium borohydride was added thereto gradually. The mixture was stirred at room temperature for one hour. 1.7 g of acetic acid were added to the reaction mixture, and said mixture was poured into water. Then, the aqueous mixture was extracted with ethyl acetate. The extract was washed with water, dried and then evaporated to remove solvent. The residue thus obtained was purified by silica gel column chromatography (Solvent: acetic acid-n-hexane (7:4)), and the eluate was evaporated to remove solvent. 0.86 g of N-benzyloxycarbonyl-α-(3,4-dimethoxyphenethylaminomethyl)-4-acetyloxybenzylalcohol was obtained as an oil.

Yield: 24.5%
IR $\nu_{max}^{liq.}$: 3460, 1760, 1700(shoulder), 1680 cm$^{-1}$
Mass m/e: 493(M+), 475 (M+-H$_2$O)
NMR (CDCl$_3$, δ): 4.88(1H, t, J=7 Hz, -CH(OH)-)

(5) 0.82 g of N-benzyloxycarbonyl-α-(3,4-dimethoxyphenethylaminomethyl)-4-acetyloxybenzylalcohol was dissolved in 30 ml of methanol, and 300 mg of 10% palladium-carbon were added thereto. The mixture was shaken at room temperature in hydrogen atmosphere for one hour under atmospheric pressure. The reaction mixture was filtered to remove the catalyst, and the filtrate was evaporated to remove solvent. Hydrochloric acid-methanol was added to the residue obtained, and the crystalline precipitates were recrystallized from a mixture of methanol and ether. 0.46 g of α-(3,4-dimethoxyphenethylaminomethyl)-4-acetyloxybenzylalcohol hydrochloride was thereby obtained as colorless needles.

Yield: 70%
M.p. 157°–160° C.
IR $\nu_{max}^{Nujol}$: 3535, 3350, 1750 cm$^{-1}$
Mass m/e: 359 (M+)
NMR (CDCl$_3$, δ): 2.25(3H, S, CH$_3$COO-)

EXAMPLE 2

0.5 g of N-benzyloxycarbonyl-α-(3,4-dimethoxyphenethylamino)-4-acetyloxyacetophenone was dissolved in 20 ml of methanol, and 0.5 g of 10% palladium-carbon was added thereto. The mixture was shaken at room temperature in hydrogen atmosphere under atmospheric pressure. After hydrogen uptake was completed, the mixture was filtered to remove the catalyst. Hydrochloric acid-methanol was added to the residue obtained, and the crystalline precipitates were recrystallized from a mixture of methanol and ether. 0.25 g of α-(3,4-dimethoxyphenethylaminomethyl)-4-acetlyoxybenzylalcohol hydrochloride was obtained as colorless needles.

Yield: 62.5% M.p. 157°–160° C.

EXAMPLE 3

(1) 4.5 g of N-benzyloxycarbonyl-α-(3,4-dimethoxyphenethylamino)-4-hydroxyacetophenone were dissolved in 20 ml of pyridine, and 2.7 g of pivaloyl chloride were added thereto. The mixture was stirred at room temperature for 4 hours. The reaction mixture was poured into ice-water and then treated in the same manner as described in Example 1-(3). 5.1 g of N-benzyloycarbonyl-α-(3,4-dimethoxyphenethylamino)-4-pivaloyloxyacetophenone were obtained as colorless needles.

Yield: 96.2%
IR $\nu_{max}^{Nujol}$: 1750, 1690 cm$^{-1}$
Mass m/e: 533(M+)
NMR (CDCl$_3$, δ): 1.35(9H, S, (CH$_3$)$_3$C—CO—)

(2) 3.0 g of N-benzyloxycarbonyl-α-(3,4-dimethoxyphenethylamino)-4-pivaloyloxyacetophenone were dissolved in a mixture of 10 ml of tetrahydrofuran and 10 ml of methanol, and 0.21 g of sodium borohydride was added thereto gradually. The mixture was stirred at room temperature for 30 minutes. Then, the reaction mixure was poured into ice-water and treated in the same manner as described in Example 1-(4). 2.5 g of N-benzyloxycarbonyl-α-(3,4-dimethoxyphenethylaminomethyl)-4-pivaloyloxybenzylalcohol were obtained as an oil.

Yield: 83.1%
IR $\nu_{max}.^{liq.}$: 3450, 1750, 1710-1660 cm$^{-1}$
Mass m/e: 535(M+)
NMR (CDCl$_3$, δ): 4.9(1H, t, C$\underline{H}$(OH))

(3) 2.23 g of N-benzyloxycarbonyl-α-(3,4-dimethoxyphenethylaminomethyl)-4-pivaloyloxybenzylalcohol, 40 ml of methanol and 0.4 g of 10% palladium-carbon were treated in the same manner as described in Example 1-(5). 1.6 g of α-(3,4-dimethoxyphenethylaminomethyl)-4-pivaloyloxybenzylalcohol hydrochloride were obtained as colorless needles.

Yield: 87.9% M.p. 150° C.
IR $\nu_{max}.^{Nujol}$: 3270, 1745 cm$^{-1}$
Mass m/e: 401(M+), 383(M+-H$_2$O)
NMR (D$_2$O, δ): 1.38 (9H, S, (C$\underline{H}_3$)$_3$C-)

EXAMPLE 4

1.0 g of N-benzyloxycarbonyl-α-(3,4-dimethoxyphenethylamino)-4-pivaloyloxyacetophenone, 40 ml of methanol and 0.75 g of 10% palladium-carbon were treated in the same manner as described in Example 2. 0.58 g of α-(3,4-dimethoxyphenethylaminomethyl)-4-pivaloyloxybenzylalcohol hydrochloride was obtained. M.p. 150° C.

EXAMPLE 5

(1) 3.0 g of N-benzyloxycarbonyl-α-(3,4-dimethoxyphenethylamino)-4-hydroxyacetophenone, 2.6 g of palmitic acid and 0.5 g of 4-dimethylaminopyridine were dissolved in 130 ml of methylene chloride, and a solution of 2.5 g of dicyclohexylcarbodiimide in methylene chloride was added thereto gradually. The mixture was stirred at 5° to 10° C. for 1.5 hours. After the reaction, insoluble materials were removed by filtration. The filtrate was evaporated to remove solvent, and the residue obtained was recrystallized from methanol. 4.0 g of N-benzyloxycarbonyl-α-(3,4-dimethoxyphenethylamino)-4-palmitoyloxyacetophenone were obtained as colorless needles.

Yield: 87.1% M.p. 84°-86° C.

(2) 2.9 g of N-benzyloxycarbonyl-α-(3,4-dimethoxyphenethylamino)-4-palmitoyloxyacetophenone were dissolved in a mixture of 20 ml of tetrahydrofuran and 2 ml of methanol, and 0.16 g of sodium borohydride was added thereto under ice-cooling. The mixture was stirred for 2 hours under ice-cooling. Then, the reaction mixture was poured into ice-water and then treated in the same manner as described in Example 1-(4). 2.1 g of N-benzyloxycarbonyl-α-(3,4-dimethoxyphenethylaminomethyl)-4-palmitoyloxybenzylalcohol were obtained as an oil.

Yield: 72.2%
IR $\nu_{max}.^{liq.}$: 3450, 1760, 1700, 1690(shoulder)
Mass m/e: 699 (M+)
NMR (CDCl$_3$, δ): 4.9 (1H, t, -C$\underline{H}$(OH)-)

(3) 2.0 g of N-benzyloxycarbonyl-α-(3,4-dimethoxyphenethylaminomethyl)-4-palmitoyloxybenzylalcohol were dissolved in 40 ml of methanol, and 0.4 g of 10% palladium-carbon was added thereto. The mixture was shaken at room temperature in hydrogen atmosphere for one hour under atmospheric pressure. The reaction mixture was filtered to remove the catalyst, and the filtrate was evaporated to remove solvent. The residue thus obtained was recrystallized from methanol. 1.8 g of α-(3,4-dimethoxyphenethylaminomethyl)-4-palmitoyloxybenzylalcohol were obtained as colorless needles.

Yield: 90.7%
M.p. 79°-81° C.
IR $\nu_{max}.^{Nujol}$: 1755 cm$^{-1}$
Mass m/e: 555(M+), 537(M+-H$_2$O)
Hydrochloride: M.p. 159° C. (recrystallized from methanol, scaly crystals)

EXAMPLE 6

0.5 g of N-benzyloxy-α-(3,4-dimethoxyphenethylamino)-4-palmitoyloxyacetophenone, 20 ml of methanol and 0, 5 g of 10% palladium-carbon were treated in the same manner as described in Example 2. 0.3 g of α-(3,4-dimethoxyphenethylaminomethyl)-4-palmitoyloxybenzylalcohol was obtained.

Yield: 69.8% M.p. 79°-81° C.

EXAMPLE 7

(1) 3.5 g of N-benzyloxycarbonyl-α-(3,4-dimethoxyphenethylamino)-4-hydroxyacetophenone were dissolved in 20 ml of pyridine, and 1.42 g of benzoyl chloride were added thereto under ice-cooling. The mixture was stirred for 2 hours. Then, the reaction mixture was poured into ice-water, and extracted with ethyl acetate. The extract was washed with 10% hydrochloric acid and water, dried and then evaporated to remove solvent. The residue obtained was crystallized in n-hexane. 4.3 g of N-benzyloxycarbonyl-α-(3,4-dimethoxyphenethylamino)-4-benzoyloxyacetophenone were obtained as colorless needles.

Yield: 99.8% M.p. 109°-111.5° C.

(2) 3.9 g of N-benzyloxycarbonyl-α-(3,4-dimethoxyphenethylamino)-4-benzoyloxyacetophenone were dissolved in a mixture of 25 ml of tetrahydrofuran and 20 ml of methanol, and 0.27 g of sodium borohydride was added thereto under ice-cooling. The mixture was stirred for 30 minutes. 0.5 ml of acetic acid was added to the reaction mixture, and said mixture was poured into ice-water. Then, the aqueous mixture was treated in the same manner as described in Example 1-(4). 3.7 g of N-benzyloxycarbonyl-α-(3,4-dimethoxyphenethylaminomethyl)-4-benzoyloxybenzylalcohol were obtained as an oil.

Yield: 95.1%
IR $\nu_{max}.^{liq.}$: 3450, 1740, 1690 cm$^{-1}$
Mass m/e: 555 (M+)
NMR (CDCl$_3$, δ): 4.9(1H, broad s, -C$\underline{H}$(OH)-)

(3) 3.7 g of N-benzyloxycarbonyl-α-(3,4-dimethoxyphenethylaminomethyl)-4-benzoyloxybenzylalcohol, 50 ml of methanol and 0.5 g of 10% palladium-carbon were treated in the same manner as described in Example 1-(5). 2.5 g of α-(3,4-dimethoxyphenethylaminomethyl)-4-benzoyloxybenzylalcohol hydrochloride were obtained as colorless needles.

Yield: 82%
M.p. 214°-216° C.
IR $\nu_{max}.^{Nujol}$: 3530, 3325, 1735 cm$^{-1}$
Mass m/e: 421 (M+), 403 (M+-H$_2$O)
NMR (DMSO-d$_6$, δ): 6.7-8.3 (12H, aromatic protons)

EXAMPLE 8

0.5 g of N-benzyloxycarbonyl-α-(3,4-dimethoxyphenethylamino)-4-benzoyloxyacetophenone, 20 ml of methanol and 0.5 g of 10% palladium-carbon were treated in the same manner as described in Example 2.

0.29 g of α-(3,4-dimethoxyphenethylaminomethyl)-4-benzoyloxybenzylalcohol hydrochloride was obtained.
Yield: 70.7% M.p. 214°–215° C.

EXAMPLE 9

(1) 3.5 g of N-benzyloxycarbonyl-α-(3,4-dimethoxyphenethylamino)-4-hydroxyacetophenone were dissolved in 20 ml of pyridine, and 1.5 g of p-toluoyl chloride were added thereto under ice-cooling. The mixure was stirred for one hour. The reaction mixture was poured into ice-water, and extracted with ethyl acetate. The extract was washed with 10% hydrochloric acid and water, dried and then evaporated to remove solvent. The residue obtained was recrystallized from methanol. 4.3 g of N-benzyloxycarbonyl-α-(3,4-dimethoxyphenethylamino)-4-p-toluoyloxyacetophenone were obtained as colorless needles.
Yield: 97.7% M.p. 122°–124° C.

(2) 4.0 g of N-benzyloxycarbonyl-α-(3,4-dimethoxyphenethylamino)-4-p-toluoyloxyacetophenone were dissolved in a mixture of 50 ml of tetrahydrofuran and 5 ml of methanol, and 0.27 g of sodium borohydride was added thereto under ice-cooling. The mixture was stirred for 30 minutes. The reaction mixture was poured into ice-water, and extracted with ethyl acetate. Then, the extract was washed with water, dried and evaporated to remove solvent. 4.17 g of N-benzyloxycarbonyl-α-(3,4-dimethoxyphenethylaminomethyl)-4-p-toluoyloxybenzylalcohol were obtained as an oil.
IR $\nu_{max.}^{liq.}$: 3450, 1740, 1710–1660 cm$^{-1}$
Mass m/e: 569 (M+)
NMR (CDCl$_3$, δ): 4.8–5.2 (1H, m, -C$\underline{H}$(OH)-)

(3) 2.5 g of N-benzyloxycarbonyl-α-(3,4-dimethoxyphenethylaminomethyl)-4-p-toluoyloxybenzylalcohol, 30 ml of methanol and 0.4 g of 10% palladium-carbon were treated in the same manner as described in Example 1-(5). 1.77 g of α-(3,4-dimethoxyphenethylaminomethyl)-4-p-toluoyloxybenzylalcohol hydrochloride were obtained as colorless needles.
Yield: 85.5%
M.p. 206°–208° C.
IR $\nu_{max.}^{Nujol.}$: 3540, 3310, 1730 cm$^{-1}$
Mass m/e: 435 (M+), 417(M+-H$_2$O)

EXAMPLE 10

0.5 g of N-benzyloxycarbonyl-α-(3,4-dimethoxyphenethylamino)-4-p-toluoyloxyacetophenone, 20 ml of methanol and 0.5 g of 10% palladium-carbon were treated in the same manner as described in Example 2. 0.3 g of α-(3,4-dimethoxyphenethylaminomethyl)-4-p-toluoyloxybenzylalcohol hydrochloride was obtained.
Yield: 71.4% M.p. 206°–208° C.

What we claim is:

1. A compound of the formula:

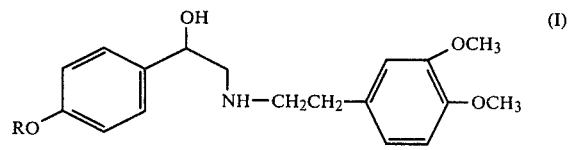

wherein R is alkanoyl of one to 20 carbon atoms, benzoyl or lower alkyl-benzoyl, or a pharmaceutically acceptable acid addition salt thereof.

2. The compound of claim 1, in which R is alkanoyl of 2 to 16 carbon atoms, benzoyl or methyl-benzoyl.

3. The compound of claim 2, in which R is acetyl, pivaloyl, palmitoyl, benzoyl or p-toluoyl.

4. The compound of claim 2, in which R is pivaloyl, benzoyl or p-toluoyl.

5. The compound of claim 1 wherein R is pivaloyl.

6. The compound of claim 1 wherein R is benzoyl.

7. The compound of claim 1 wherein R is toluoyl.

8. The compound of claim 7 wherein R is p-toluoyl.

9. A cardiotonic composition comprising an effective amount of a compound of claim 1 or a pharmaceutically acceptable acid addition salt thereof and a pharmaceutically acceptable carrier.

* * * * *